US007125957B1

(12) United States Patent
Aida et al.

(10) Patent No.: US 7,125,957 B1
(45) Date of Patent: Oct. 24, 2006

(54) VPR MUTANT PROTEIN AND ITS ENCODING GENE HAVING APOPTOSIS-INDUCING ACTION

(75) Inventors: Yoko Aida, Ibaraki (JP); Masakazu Kamata, Ibaraki (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/787,437

(22) PCT Filed: Jan. 29, 1999

(86) PCT No.: PCT/JP99/00388

§ 371 (c)(1),
(2), (4) Date: Jun. 25, 2001

(87) PCT Pub. No.: WO00/18426

PCT Pub. Date: Jun. 4, 2000

(30) Foreign Application Priority Data

Sep. 30, 1998 (JP) ................................. 10/277361

(51) Int. Cl.
*A61K 38/00* (2006.01)
(52) U.S. Cl. .................. 530/324; 536/23.72; 530/826; 514/2; 514/44
(58) Field of Classification Search .............. 536/23.72; 530/324, 826; 514/2, 44; 424/188.1, 208.1
See application file for complete search history.

(56) References Cited

OTHER PUBLICATIONS

Piller et al. "Vpr protein of human immunodeficiency virus type 1 forms cation-selective channels in planar lipid bilayers", Proceedings of the National Academy for Sciences of the United States of America, (Jan. 9, 1996) 93 (1) 111-5.*
Lavallee et al. "HIV-1 HxBc2 strain encodes a truncated vpr gene product of 78 amino acids" Journal of acquired immune deficiency syndromes, (May 1993) 6 (5) 529-30.*
Yuan et al., "Human immunodeficiency virus vpr gene encodes a virion-associated protein", AIDS research and human retroviruses, (Nov. 1990) 6 (11) 1265-71.*
Dedera et al. "Virus protein R of human immunodeficiency virus types 1 and 2 is dispensable for replication and cytopathogenicity in lymphoid cells", Journal of virology, (Jul. 1989) 63 (7) 3205-8.*
Riffkin et al. "A single amino-acid change between the antigenically different extracellular serine protease V2 and B2 from *Dichelobactor nodous*". Gene (1995) vol. 167, pp. 279-283.*
Ngo et al., in The Protein Folding Problem and Tertiary Structure Prediction, 1994, Edited by Merz et al., (ed.), Birkhauser Boston, MA pp. 433 and 492-495.*
J.F. Kerr et al., "Apoptosis: A Basic Biological Phenomenon with Wide-Ranging Implications in Tissue Kinetics", BR. J. Cancer, vol. 26, pp. 239-257 (1972).
Akio Adachi et al., "Production of Acquired Immunodeficiency Syndrome-Associated Retrovirus in Human and Nonhuman Cells Transfected with an Infectious Molecular Clone", Journal of Virology, vol. 59, No. 2, pp. 284-291 (1986).
Wilfried Kramer et al., "Oligonucleotide-Directed Construction of Mutations via Gapped Duplex DNA", in Methods in Enzymology, vol. 154, pp. 350-367 (1987).
Basic Methodology in PCR Technology, pp. 1-5 (Erlich editor, Stockton Press 1989).
Ayyavoo et al., "HIV-1 Vpr Suppresss Immune Activation and Apoptosis Through Regulation of Nuclear Factor Kappa B." Nat. Med. (N.Y.) vol. 3, No. 10, pp. 1117-1123 (1997).
Stewart et al., "Human Immunodeficiency Virus Type Vpr Induces Apoptosis Following Cell Cycle Arrest." J. Virol. vol. 71, No. 7, pp. 5579-5592 (1997).
Arunagiri al., "A C-terminal Domain of HI-1 Accessory Protein Vpr is Involved in Penetration, Mitochondrial Dysfunction and Apoptosis of Human CD4+Lymphocytes."Apoptosis, vol. 2, No. 1, pp. 69-76 (1997).
He, Jianglin et al., "Human Immunodeficiency Virus Type 1 Viral Protein R (Vpr) Arrest Cells in the G2 Phase of the Cell Cycle by Inhibiting p34cdc2 Activity." J. Virol. vol. 69, No. 11, pp. 6705-6711 (1995).
Jowett, Jeremy et al., "The Human Immunodeficiency Virus Type 1 Vpr Gene Arrest Infected T Cell in the G2+M phase of the Cell Cycle." J. Virol. vol. 69, No. 10, pp. 6304-6313 (1997).
Aida, "Human Immunodeficiency Virus Type 1 VPR Gene Product Prevents Cells Proliferation", RIKEN Review, No. 18, Aug. 1998, pp. 37-38.
Nishizawa et al., "Apoptosis Induction by a Deficient Mutant of HIV-1 VPR Gene", Program and Abstract of the 46th General Meeting of the Japanese Society for Virology, Oct. 12-14, 1998 With partial English language translation of the same.

* cited by examiner

*Primary Examiner*—Jeffrey Stucker
(74) *Attorney, Agent, or Firm*—Greenblum & Bernstein, P.L.C.

(57) ABSTRACT

An apoptosis inducing agent which comprises a protein as being Vpr protein encoded by vpr gene of HIV-1 wherein 15 amino acid residues from the C-terminal are deleted, and an apoptosis inducing gene encoding said protein. The agent induces apoptosis of cells and therefore useful as a medicament for treatment of a cancer or AIDS.

5 Claims, No Drawings

SEQUENCE LISTING

<160> NUMBER OF SEQ ID NOS: 2

<210> SEQ ID NO 1
<211> LENGTH: 28
<212> TYPE: DNA
<213> ORGANISM: Artificial
<220> FEATURE:
<223> OTHER INFORMATION: Artificial Sequence
<220> FEATURE:
<221> NAME/KEY: PCR Primer
<222> LOCATION: (1)..(28)
<223> OTHER INFORMATION: Sense primer

<400> SEQUENCE: 1
gaagatatcc gaacaagccc cagaagac                28

<210> SEQ ID NO 2
<211> LENGTH: 30
<212> TYPE: DNA
<213> ORGANISM: Artificial
<220> FEATURE:
<223> OTHER INFORMATION: Artificial Sequence
<220> FEATURE:
<221> NAME/KEY: PCR Primer
<222> LOCATION: (1)..(30)
<223> OTHER INFORMATION: Anti-sense Primer

<400> SEQUENCE: 2
ggtctagatc atattctgct atgtcgacac                30

VPR MUTANT PROTEIN AND ITS ENCODING GENE HAVING APOPTOSIS-INDUCING ACTION

TECHNICAL FIELD

The present invention relates to a protein having an apoptosis-inducing action and a gene encoding said protein.

BACKGROUND ART

Apoptosis is cell death that occurs under various physiological conditions, which differs from necrosis occurring due to physical injuries, chemical toxicants and so forth (Kerr, J. F. and Wyllie, A. H., Br. J. Cancer, 26, pp. 239–257, 1972), and is also referred to as programmed cell death. Apoptosis is induced by cell damages by cytotoxic T cells, radiation irradiation, cytokines such as tumor necrosis factor (TNF), anti-CD3 antibodies and so forth, and apoptosis is also observed in spontaneous regression of malignant tumors. It is expected that gene therapies and destruction of specific cancer cells will become possible by using a gene or a gene product exogenously inducing cell apoptosis.

Human immunodeficiency virus type 1 (HIV-1), the causative virus of human acquired immunodeficiency syndrome (AIDS), has accessory genes (nef, vpr, vpu, and vif) which are not essential for its own replication in addition to the structural genes and regulatory genes. A gene product of vpr (protein Vpr), one of the accessory genes, has been focused as a key factor for the onset of AIDS since, for example, it increases virus infection efficiency and triggers production of viruses from latent HIV infected cells. Moreover, it has also been elucidated that the protein Vpr has a wide variety of physiological actions such as inhibition of cell growth, induction of differentiation, induction of apoptosis, inhibition of apoptosis and induction of nucleus polyploidization.

DISCLOSURE OF THE INVENTION

An object of the present invention is to provide a gene having apoptosis-inducing action and a gene product thereof. The inventors of the present invention conducted various studies to achieve the aforementioned object. As a result, they found that a mutant, in which 15 amino acid residues were deleted from the carboxyl terminal of Vpr protein consisting of 96 amino acid residues encoded by vpr as the accessory gene of HIV-1, had extremely high apoptosis-inducing activity, and thereby exhibited suppressing activity on cell proliferation. The present invention was achieved on the basis of these findings.

The present invention thus provides an apoptosis inducing agent which comprises a protein as being Vpr protein encoded by vpr gene of HIV-1 in which 15 amino acid residues from C-terminal are deleted. From another aspect of the present invention, there is provided an apoptosis inducing agent which comprises a protein having the amino acid sequence of the aforementioned protein wherein one to several amino acids are substituted, inserted, and/or deleted, and having apoptosis-inducing activity. The present invention also provides an apoptosis-inducing gene encoding the aforementioned protein.

From further aspects of the present invention, there are provided a method for inducing cell apoptosis by using the aforementioned protein or the aforementioned gene; a recombinant vector comprising the aforementioned gene; and a method for inducing cell apoptosis by using the aforementioned recombinant vector.

As a still further aspect of the present invention, there is provided a medicament comprising the aforementioned protein as an active ingredient. The medicament comprising said protein as an active ingredient is useful as, for example, a anticancer agent or anti-AIDS agent. There is also provided a medicament comprising the recombinant vector as an active ingredient. The medicament can be used for a gene therapy of a cancer or AIDS. The present invention further provides a method for treating a cancer or AIDS which comprises the step of administering an effective amount of the aforementioned protein or the aforementioned recombinant vector to a patient, and use of the aforementioned protein or the aforementioned gene for a manufacture of the aforementioned medicament.

BEST MODE FOR CARRYING OUT THE INVENTION

The protein of the present invention is composed of 81 amino acid residues, which is Vpr protein encoded by vpr gene of HIV-1 in which 15 amino acid residues from the C-terminal are deleted (hereafter, this protein is also referred to as "C81 mutant protein" in the specification). This C81 mutant protein can be easily prepared according to the method described in the example mentioned below. The C81 mutant protein can also be prepared by utilizing the nucleic acid sequences of the vpr gene of HIV-1 or the amino acid sequence of the Vpr protein (Adachi, A. et al., J. Virol., 59, pp. 284–291, 1986).

The C81 mutant protein of the present invention is characterized by markedly increased apoptosis-inducing action compared to the Vpr protein. The increased apoptosis-inducing action of the C81 mutant protein of the present invention can easily be determined by those skilled in the art according to the method of the example in the specification. In addition, the protein of the present invention is characterized to have substantially no ability to arrest cells in the $G_2$ phase, unlike the Vpr protein.

A protein which has the amino acid sequence of the aforementioned C81 mutant protein wherein one to several amino acid residues are substituted, inserted, and/or deleted and has apoptosis-inducing action similar to that of the C81 mutant protein also falls within the scope of the present invention (hereinafter referred to as a "modified protein"). Both DNA and RNA sequences comprising a nucleic acid sequence coding for the C81 mutant protein or a modified protein fall within the scope of the gene of the present invention. The genes can be easily obtained according to the method described in the aforementioned reference.

The aforementioned modified protein can be prepared by subjecting *Escherichia Coli* or the like having a DNA encoding the amino acid sequence of the C81 mutant protein to a treatment for mutation by using an agent such as N-nitro-N'-nitro-N-nitrosoguanidine, collecting a gene encoding a modified protein from the microbial cells, and then performing conventional procedure for gene expression. It is also possible to directly introduce deletion, substitution, or addition of nucleotides into the aforementioned gene by directly treating the gene with an agent such as sodium sulfite, or applying site-directed mutagenesis (Kramer, W. et al., Methods in Enzymology, 154, p. 350, 1987), recombinant PCR method (PCR Technology, Stockton press, 1989) or the like.

The protein of the present invention is useful as an apoptosis inducing agent. For example, the protein can be used as a medicament for inducing apoptosis in cancer cells to kill the cells. The protein is also useful for elimination of latent infected cells with human immunodeficiency virus (HIV) and development of techniques for the elimination. Therefore, the medicament comprising the protein of the present invention can be used for preventive and/or therapeutic treatment of a cancer or preventive and/or therapeutic treatment of acquired immunodeficiency syndrome (AIDS). A method for administration, a dose, a dosage form and so forth of the medicament of the present invention can be appropriately selected by those skilled in the art and are not particularly limited.

For the purpose of utilization as the aforementioned medicament, the protein of the present invention may be fused with other polypeptide. Fusion proteins containing the amino acid sequence of the protein of the present invention as a partial sequence and genes coding for such fusion proteins also fall within the scope of the present invention. For example, it becomes possible to specifically induce apoptosis in target cells such as cancer cells by preparing a protein fused with a monoclonal antibody or a fragment thereof specifically recognizing the target cells. The protein of the present invention is also expected to be useful in treatment of diseases associated with apoptosis resistance, and is useful as a reagent in the fields of biochemistry, genetic engineering and so forth.

The gene of the present invention is useful for preparing the protein of the present invention, as well as for gene therapy of diseases associated with apoptosis resistance. For example, the gene can be used for gene therapy for preventive and/or therapeutic treatment of a cancer or AIDS. Procedures for the gene therapy are not particularly limited, and in general, the gene of the present invention is inserted into a vector, and then the recombinant vector is introduced into a living body for expression of the gene of the present invention. Various vectors for introducing the gene into living bodies are known, and those skilled in the art can chose an appropriate vector. Techniques for regulating expression of a gene in a specific cell are also available for those skilled in the art. In addition, HIV infected cells can be directly and specifically destroyed by ligating the gene of the present invention to a region downstream from HIV-1 LTR, and then introducing the resulting gene into a living body after the gene is encapsulate in liposomes modified with anti-HIV gp120 antibody.

EXAMPLE

The present invention will be more specifically explained with reference to the following example. However, the scope of the present invention is not limited to the following example.

1. Materials and Methods

A Flag sequence was ligated to the 5' end of vpr gene fragment of HIV-1 infectious DNA clone pNL432 and inserted into high-level expression vector pME18neo. This procedure will be explained below.

(1) Primers designed for amplifying a gene coding for the C81 mutant protein (hereafter, referred to as "C81 mutant gene") were as follows:

Sense Primer: 5'-GAA<u>GATATC</u>CGAACAAGCCCCAGAAGAC-3' (SEQ ID NO: 1)

Anti-sense Primer: 5'-GG<u>TCTAGA</u>TCATATTCTGCTATGTCGACAC-3' (SEQ ID NO: 2)

In addition to a cohesive sequence, an EcoRV site for ligation of Flag-Tag was added to the 5' end of the sense primer, and an XbaI site for ligation of subcloning vector was added to the 3' end of the anti-sense primer (restriction sites are underlined). PCR was performed by using these primers and using an infectious DNA clone pNL432 of HIV-1 isolate NL43 (Adachi, A. et al., J. Virol., 59, pp. 284–291, 1986) as a template to amplify the C81 mutant gene fragment.

(2) After heat denaturation in a reaction solution containing 1 µg of the template DNA, PCR buffer (10 mM Tris-HCl, pH 8.3, 50 mM KCl, 1.5 mM $MgCl_2$, 0.001% gelatin), 0.2 mM dNTP, 50 pmol each of the primers, and 2.5 units of Ampli Taq polymerase (Perkin Elmer Cetus) at 94° C. for 5 minutes, amplification was performed by 35 cycles of reaction at 94° C. for 1 minute, at 54° C. for 1 minute, and at 72° C. for 2 minutes. Then, extension reaction was performed at 72° C. for 10 minutes. The resulting PCR product was treated with EcoRV and XbaI for 4 hours or more, and the resulting DNA was fractioned by agarose gel electrophoresis. Then, the target DNA fragment was eluted and purified by using a GENECLEAN II KIT.

(3) Fro ligation of the amplified fragment and the Flag-Tag sequence, the vpr gene fragment amplified by PCR was then ligated to pBluescript SK+–II vector ligated beforehand with Flag-Tag and treated with EcoRV and XbaI, and transformed into *Escherichia Coli* competent cells XLI-Blue. Then, a DNA fragment of the C81 mutant gene was excised from the Fvpr/pBluescript SK+–II at the NotI and XhoI cleavage sites. The target DNA fragment was eluted by using the GENECLEAN II KIT, ligated to pME18Neo, and then introduced into XLI-Blue to obtain transformed cells. The plasmid DNA was prepared by the SDS method and purified by the cesium chloride equilibrium density gradient centrifugation method.

Each of the above plasmid, wild-type vector, and a control vector was introduced into HeLa cells by electroporation. Effect on cell growth was analyzed by the colony formation method. Twelve hours after the introduction, $5 \times 10^5$ cells were placed in a 10-cm petri dish and cultured in a selective medium containing G418 for 12 days. After fixation with methanol, giemsa staining was performed and the number of colonies was counted. At this time, introduction efficiency was calculated for each mutant by the β-Gal staining and the number of colonies was corrected. The cell cycle was analyzed by flow cytometry.

The C81 mutant gene expression plasmid was transiently co-introduced with the GFP expression plasmid. After 48 hours, the cell was fixed by using 1% formamide/PBS and then 70% methanol, stained with a PI staining solution and analyzed by FACS. Cells introduced with C81 mutant gene and non-introduced cells were distinguished by using fluorescence of GFP as a marker, and the DNA content in each fraction was examined. The cells were classified into + those having ability to arrest cells in $G_2$ comparable to the wild-type; ± weaker than the wild-type, and − no ability. Similarly, 48 hours after the introduction, the cells were stained by dual fluorescent staining using anti-Flag antibodies or anti-minichromosome maintenance (MCM) antibodies and then investigated under a confocal laser microscope. MCM negative cells were determined as cells in the $G_2$ phase.

To detect growing cells, the cells were cultured in the presence of bromodeoxyuridine (BrdU) for 30 minutes and then subjected to fluorescent staining using anti-BrdU antibodies. Further, 48 hours after the introduction, the cells were subjected to fluorescent staining by using biotin-labeled annexin V and PE-labeled streptavidin. The cells were observed under a confocal laser microscope by using GFP positive cells as a marker of the cell introduced with C81 mutant gene. Annexin V positive cells were determined as apoptosis-induced cells.

2. Results

In the HeLa cells introduced with the C81 mutant gene encoding the C81 mutant protein, which corresponded to the Vpr protein with deletion of 15 amino acid residues from the C-terminal, the ability of forming colonies was reduced about 30% compared to the cells introduced with the control vector, even though the $G_2$-phase arrest was not observed. The uptake of BrdU by the cells introduced with the vpr having the C-terminal deletion was also markedly reduced compared to the cells introduced with the control vector. Further, fluorescent staining of the cells using anti-serum for MCM as the $G_2$-phase marker revealed that the above suppressing action against cell proliferation was not induced by the $G_2$-phase arrest.

From the above results, it was verified that the cell proliferation was markedly suppressed in the cells introduced with the Vpr having the C-terminal deletion by a mechanism different from the $G_2$-phase arrest. For further investigation, the cells were stained with annexin V/biotin. As a result, remarkable and rapid increase of the proportion of cells under apoptosis was observed in the cells introduced with the Vpr having the C-terminal deletion compared to the cells introduced with the wild-type Vpr. Thus, it was revealed that the mutant Vpr protein having deletion of 15 amino acid residues at the carboxyl terminal had remarkably high apoptosis inducing activity.

TABLE 1

| Examined Item | Type of cells introduced with expression vector | | |
|---|---|---|---|
| | C81 mutant | Wild type | Control vector |
| $G_2$-phase arrest[1] | − | + | − |
| Percentage of positive cells in fluorescent staining with anti-MCM antibody[2] | 63.6% | 18.3% | 80.0% |
| Colony forming ability[3] | 72.8% | 7.6% | 100.0% |
| Percentage of cells taking up BrdU[4] | 20.1% | 19.5% | 34.8% |
| Percentage of positive cells in staining with annexin V/biotin[5] | 20.7% | 1.4% | 1.3% |

[1] +: having ability of arresting cells in the $G_2$ phase comparable to the wild-type, ±: weaker than the wild-type, −: no ability of arresting cells in the $G_2$ phase.
[2] MCM negative: cell in the $G_2$ phase
[3] The introduction efficiency was calculated for each mutant by using β-Gal staining to correct the number of colonies. Values are indicated as % based on the number of colonies of the cells introduced with the control vector, which is taken as 100.
[4] Anti-BrdU antibody positive: cells under proliferation
[5] Annexin V positive: cells under apoptosis induction

What is claimed is:

1. An apoptosis inducing agent which comprises an isolated Vpr protein encoded by Vpr gene of HIV-1 wherein 15 amino acid residues from the C-terminal are deleted.

2. The apoptosis inducing agent according to claim 1, which comprises said protein having substantially no ability of arresting a cell in $G_2$ phase.

3. An isolated apoptosis-inducing gene encoding the protein according to claim 1.

4. A recombinant vector containing the gene according to claim 3.

5. An isolated apoptosis-inducing gene encoding the protein according to claim 2.

* * * * *